US006323166B1

(12) United States Patent
Kamiya

(10) Patent No.: US 6,323,166 B1
(45) Date of Patent: Nov. 27, 2001

(54) SHAMPOO COMPOSITIONS

(75) Inventor: Akira Kamiya, 2-44, Misumi-cho, Chigasaki-shi, Kanagawa-ken (JP)

(73) Assignee: Akira Kamiya, Kanagawa-Ken (JP)

( * ) Notice: Subject to any disclaimer, the term of this patent is extended or adjusted under 35 U.S.C. 154(b) by 0 days.

(21) Appl. No.: 09/356,418

(22) Filed: Jul. 16, 1999

(30) Foreign Application Priority Data

Jul. 22, 1998 (JP) .................................................. 10-222302
Feb. 15, 1999 (JP) .................................................. 11-035623

(51) Int. Cl.⁷ .............................. A61K 7/075; C11D 1/10
(52) U.S. Cl. ........................ 510/119; 510/123; 510/129; 510/130; 510/433; 510/499; 424/70.1; 424/70.19
(58) Field of Search ..................................... 510/119, 123, 510/129, 130, 433, 499; 424/70.1, 70.19

(56) References Cited

U.S. PATENT DOCUMENTS 4,919,846 * 4/1990 Nakama et al. ...................... 252/542
5,374,614 * 12/1994 Behan et al. ............................. 512/3
5,648,323 * 7/1997 Coffindaffer et al. ................. 510/122
5,833,999 * 11/1998 Trinh et al. ........................... 424/401
5,874,073 * 2/1999 Kaiser et al. ...................... 424/70.11

\* cited by examiner

*Primary Examiner*—Yogendra N. Gupta
*Assistant Examiner*—Brian P. Mruk
(74) *Attorney, Agent, or Firm*—Roylance, Abrams, Berdo & Goodman, L.L.P.

(57) ABSTRACT

A shampoo composition for removing minute chemicals deposited on the skin, softening the hair, giving a rinsing effect and controlling dandruff and itch on the scalp is provided.

Said composition comprises (a) 0.05–5.0% by weight of an essential oil component selected from the group consisting of terpene esters and terpene hydrocarbons, (b) 3.0–20% by weight of an N-acylamino acid salt and (c) 0.1–15.0% by weight of a sucrose fatty acid ester or a $C_6$–$C_{18}$ fatty acid alkylolamide.

16 Claims, No Drawings

SHAMPOO COMPOSITIONS

BACKGROUND OF THE INVENTION

The present invention claims the priority of Japanese Patent Application Nos. 10-222302 filed Jul. 22, 1998 and 11-35623 filed Feb. 15, 1999 which are incorporated herein by reference.

The present invention relates to shampoo compositions for cleaning the head and body, softening the hair, giving a rinsing effect and improving atopic dermatitis (including bath shampoo compositions).

Recently, the presence of a disease called "chemical hypersensitivity" has been reported. This disease manifests itself to involve vegetative disorder, headache, melancholia, nausea, etc. when the total uptake of chemicals exceeds a certain level. Another disease called "sick house syndrome" has also been reported, which is caused by the interior air contaminated with building materials or coatings in newly built or rebuilt houses. These diseases are caused by several tens of thousands or more types of chemicals produced.

Dirt on the skin includes fats, sweat and dead keratin resulting from skin metabolism as well as minute chemicals contained in dust as described above, allergens and chemicals contained in skin detergents or rinses, hair-setting sprays and like daily products. These chemicals deposited on the skin are believed to cause atopic dermatitis. These minute chemicals penetrate the interstices between the epidermal keratin just before exfoliation and the underlying keratin to transcutaneously have an adverse influence on human bodies. Even those who have not developed atopic dermatitis may show conditions thereof when the total uptake of chemicals exceeds a certain level.

Therefore, people of the present generation are required to remove these minute chemicals from the skin.

These minute chemicals entered between keratins can not be removed with surfactants alone. Petroleum surfactants induce denaturation of protein while soaps consisting of fatty acid salts are not preferable for application to affected skin because of their alkalinity. Natural fat-derived detergents such as N-acylated amino acid surfactants or sugar esters do not irritate the skin, but their detergency is low.

Quaternary ammonium surfactants such as dialkyldimethylammonium chloride conventionally used for softening the hair promote skin roughening. Rinse-in-shampoos recently available on the market are dubious in terms of safety.

The present invention proposes a shampoo composition for removing minute chemicals deposited on the skin responsible for atopic dermatitis as described above, and also softening the hair, giving a rinsing effect and controlling dandruff and itch on the scalp.

SUMMARY OF THE INVENTION

The present invention provides a shampoo composition comprising (a) 0.05–5.0% by weight of an essential oil component selected from the group consisting of terpene esters and terpene hydrocarbons (including essential oil components selected from the group consisting of linalool, citronellol, nerol, terpineol, geraniol and cineole), (b) 3.0–20% by weight of an N-acylamino acid salt and (c) 0.1–15.0% by weight of a sucrose fatty acid ester or $C_6$–$C_{18}$ fatty acid alkylolamide, on the basis of the total weight of the composition.

The ratio of said (a) to (b) is 1:2–1:120, preferably 1:9–1:80.

DETAILED DESCRIPTION OF THE INVENTION

Terpene esters, terpene hydrocarbons and other essential oil components used in the present invention are isolated or synthesized essential oil components capable of dissolving chemical fine powder and fats. These terpene esters or terpene hydrocarbons generally have analgesic, rot-proof, antibacterial and antiviral effects on the skin, and are orally and transcutaneously innocuous, non-neurotoxic upon inhalation and internally metabolized. These components are used in the range of 0.05 to 5.0% by weight, preferably 0.1 to 1.0% by weight.

Terpene esters have been found to be generally innocuous, non-irritatave and non-sensitizable, have antibacterial and anti-inflammatory effects and have their components safely metabolized after transcutaneous penetration. Among terpene esters, monoterpene esters are preferred. Specific compounds include acetate esters such as linalyl acetate, geranyl acetate, benzyl acetate, bornyl acetate, terpinyl acetate, citronellyl acetate, eugenyl acetate or neryl acetate, citronellyl formate, isobutyl angelicate, methyl anthranilate or methyl cinnamate, preferably linalyl acetate, geranyl acetate or bornyl acetate.

Essential oils per se are not used in the present invention, because they may contain toxic components and have varying compositions dependent on the place or year of production and so it is difficult to check their safety.

Terpene hydrocarbons may be used in place of or in addition to terpene esters of the present invention because they dissolve fats and synthetic products, among which pinenes are especially preferred because they mildly dissolve fats and synthetic products. They are preferably combined with natural vitamin E as an antioxidant because they somewhat irritate the skin when they are oxidized. Terpene hydrocarbons include monoterpene hydrocarbons, sesquiterpene hydrocarbons and diterpene hydrocarbons, etc., preferably monohydrocarbons, most preferably α- or β-pinene, d-limonene, terpinene because of their high safety.

Other terpenes than terpene esters and terpene hydrocarbons, which can be used in addition to said terpene esters or terpene hydrocarbons, include terpene alcohols such as linalool, citronellol, nerol, terpineol, geraniol. Cineole can also be used. These components have the ability to dissolve fats but not synthetic products, so that they are used to control the detergency, which could not be controlled by surfactants.

Among said essential oil components, α-pinene, d-limonene, bornyl acetate and linalyl acetate have good effects without unpleasant odor. Especially, α-pinene is preferable because of mildness and good balance between dissolving powers for chemical fine powder and for fats.

α- or β-pinene and d-limonene can readily be solubilized in triethanolamine N-cocoyl DL-alanine especially in the presence of a sucrose fatty acid ester or a coconut fatty acid diethanolamide to form a clear shampoo. Linalyl acetate, geranyl acetate, bornyl acetate and citronellyl acetate can readily be solubilized in triethanolamine N-cocoyl DL-alanine in the presence of a coconut fatty acid diethanolamide to form a clear shampoo. If an N-acyl fatty acid L-glutamic acid salt is used, essential oil components will be translucent, gelled or creamed. According to the present invention, essential oil components appear clear in acidic medium but not in basic medium.

Now, the N-acylamino acid salt of the present invention is described in which are emulsified, creamed, solubilized, gelled or dispersed terpene esters, hydrocarbons or the like used in the present invention.

N-Acylamino acid salts are known to cause no denaturation of protein and have skin protection effect and bacteriostatic effect. We discovered that N-acylamino acid salts readily solubilize terpene esters or the like to readily convert them into solution, gel or cream. In the present invention, N-acylamino acid salts can be used in the amount of 3.0–20.0% by weight, preferably 6.0–15.0% by weight.

The amino acid in the N-acylamino acid salt is not specifically limited, but preferably hydrophilic acidic amino acids such as L-glutamic acid, L-aspartic acid; and basic amino acids such as L-arginine, L-lysine. Most preferred amino acids include aliphatic amino acids such as DL-alanine, DL-glycine. The fatty acid forming N-acyl includes coconut fatty acid, stearic acid, myristic acid, palmitic acid, oleic acid, linoleic acid, linolenic acid, lauric acid, tridecyl acid, pentadecyl acid, heptadecyl acid, nonadecanoic acid, arachic acid and behenic acid, preferably $C_6$–$C_{18}$ fatty acids, more preferably coconut fatty acid. Salts thereof include sodium salts, potassium salts or triethanolamine salts, etc. Specific compounds of N-acylamino acid salts include triethanolamine N-cocoyl DL-alanine, N-cocoyl L-glutamic acid salts (including sodium salt, disodium salt, potassium salt, dipotassium salt, triethanolamine salt, etc., among which dipotassium salt and triethanolamine salt are stable; terpene alcohols form solutions therein), triethanolamine N-lauroyl L-glutamate, sodium N-lauroyl L-glutamate, potassium N-lauroyl L-glutamate, sodium N-myristoyl glutamate, potassium N-myristoyl glutamate, disodium N-stearoyl glutamate, sodium N-stearoyl L-glutamate (terpene alcohols form creams therein), sodium N-cocoyl sarcosine, triethanolamine N-lauroyl sarcosine, sodium N-cocoyl DL-alanine, sodium N-cocoyl glycine, sodium N-cocoyl arginine, sodium N-cocoyl glutamate, sodium N-stearoyl glutamate, sodium N-cocoyl alanine, potassium N-cocoyl glycine (terpene alcohols form gels therein), sodium N-cocoyl arginine, sodium N-oleoyl glutamate, sodium N-oleoyl alanine, sodium N-oleoyl glycine, sodium N-oleoyl arginine and sodium N-lauroyl arginine, etc.

In combination with the N-acylamino acid salt, a fatty acid alkylol amide or a sucrose fatty acid ester is added as a solubilizing cosolvent. The fatty acid in both contains 6 to 8 carbon atoms, and the fatty acid in the sucrose fatty acid ester preferably includes coconut fatty acid, stearic acid, palmitic acid or oleic acid. A specific compound is sucrose cocoate. The fatty acid alkylol amide includes coconut fatty acid monoethanolamide, coconut fatty acid diethanolamide, myristic monoethanolamide, myristic diethanolamide, lauric diethanolamide, lauric monoethanolamide, preferably coconut fatty acid diethanolamide. When an N-acylamino acid salt and a coconut fatty acid diethanolamide are used in combination to solubilize a terpene alcohol, the resulting solution becomes a "clear solution" irrespective of the nature of the amino acid. The amount of the fatty acid alkylol amide or sucrose fatty acid ester to be used ranges from 0.1 to 15.0% by weight, preferably 1.0 to 10% by weight.

For use on the scalp, compositions may further contain vitamin E or a derivative thereof as a capillary dilating component for promoting blood circulation.

Shampoo compositions of the present invention may contain polysaccharides, glycerin, sodium lactate, D-sorbitol, chitin-chitosan, urea, pyrrolidone carboxylic acid or a salt thereof as a thickener to control the balance between the dissolving powers of the shampoo compositions of the present invention for chemical fine powder and for fats, thus making the detergency milder. These additives may also act as skin protecting agents. Particularly, polysaccharides have dual effects by acting as an antioxidant for terpene hydrocarbons in combination with an N-acylamino acid and making the solution milder by changes with time to improve smoothness. Polysaccharides include natural guar gum, locust bean gum, quince seed, carrageenan, galactan, gum arabic, tragacanth gum, pectin, mannan and starches, xanthan gum, dextran, succinoglucan, hyaluronic acid, semisynthetic methyl cellulose, ethyl cellulose, hydroxypropyl cellulose, hydroxyethyl cellulose, carboxymethyl cellulose, methylhydroxypropyl cellulose, sodium alginate, propylene glycol alginate ester, etc. Proteins such as gelatin, casein, albumin, collagen may also be used. Polysaccharides can be used at 0.1–2.0% by weight, preferably 0.2–1.0% by weight, while glycerin, D-sorbitol, sodium lactate and chitin-chitosan can be used at 0.5–10% by weight, preferably 1.0–5.0% by weight.

Either one or a combination of citric acid salts and potassium aluminium sulfate can be used as a dispersion stabilizer for polysaccharides. These compounds avoid the necessity of using petroleum solvents such as propane diol, butane diol, isobutane diol, pentane diol, isopentane diol, neopentane diol or derivatives thereof. Such citric acid salts or the like also act as a thickener. Citric acid salts can be used at 0.5–10% by weight, preferably 1.0–5.0% by weight, while potassium aluminium sulfate can be used at 0.5–5% by weight, preferably 1.0–3.0% by weight. These citric acid salts or the like also act as a skin protecting agent and also have a preservative effect.

Shampoo compositions of the present invention can contain preservatives such as sorbic acid.

For use as a skin cleansing cream, especially for removing makeup, compositions of the present invention may also contain natural liquid oily components such as jojoba oil, sweet almond oil, grape seed oil, olive oil, sesame oil, coconut oil, evening primrose oil, wheat germ oil, apricot kernel oil, avocado oil, macadamia nut oil, rose hip oil, carrot seed oil, calendula oil, St.-John's-wort oil, camellia oil, oleic acid, squalane; or natural solid oily components such as beeswax, stearic acid. This cleansing cream may contain ethanol for disinfection. The ratio between the oily phase and the aqueous phase (including ethanol) ranges from 1:9 to 9:1, preferably 1:4 to 4:1.

The following examples further illustrate the present invention without, however, limiting the same thereto.

EXAMPLES

Examples 1–17 and Comparative examples 1 and 2

Shampoos having the compositions shown in Table 1 (the values in the table are expressed in grams) were prepared. Water was added to each formulation to 100 ml.

Results are shown in Tables 1 and 2.

TABLE 1

|  | Examples | | | | | | | | | | | Comparative example |
|---|---|---|---|---|---|---|---|---|---|---|---|---|
|  | 1 | 2 | 3 | 4 | 5 | 6 | 7 | 8 | 9 | 10 | 11 | 1 |
| α-Pinene | 0.2 | | | | | | | | | | | 1 |
| d-Limonene | | 0.1 | | | | | | | | | | |
| Dipentene T | | | 0.1 | | | | | | | | | |
| γ-Terpinene | | | | 0.3 | | | | | | | | |
| Linalyl acetate | | | | | 0.4 | | | | | | | |
| Bornyl acetate | | | | | | 0.2 | | | | | | |
| Geranyl acetate | | | | | | | 0.1 | | | | | |
| Benzyl acetate | | | | | | | | 0.1 | | | | |
| Citronellyl acetate | | | | | | | | | 0.15 | | | |
| Methyl angelicate | | | | | | | | | | 0.1 | | |
| 1,8-Cineole | | | | | | | | | | | 0.1 | |
| Guar gum | 0.5 | | | | 0.5 | | | | 0.5 | | | 0.5 |
| Xanthan gum | | | 0.5 | | | | | | | | | |
| Sucrose cocoate | 1.0 | 1.0 | | | | | | | | | | |
| Coconut fatty acid diethanolamide | | | 2.0 | 2.0 | 2.0 | 2.0 | 2.0 | 2.0 | 2.0 | 2.0 | 2.0 | |
| Triethanolamine N-cocoyl DL-alanine | 9.0 | 9.0 | 9.0 | 9.0 | 9.0 | 9.0 | 9.0 | 9.0 | 9.0 | 9.0 | 9.0 | 12.0 |
| Evaluation of hair softening and needlessness of rinses | ○ | ○ | ○ | ○ | ○ | ○ | ○ | ○ | ○ | ○ | ○ | x |
| Evaluation after shampooing | ○ | ○ | ○ | ○ | ○ | ○ | ○ | ○ | ○ | ○ | ○ | x |
| Evaluation of removal of hair spray deposited on the skin | ○ | ○ | ○ | ○ | ○ | ○ | ○ | ○ | ○ | ○ | ○ | x |
| Evaluation of removal of scale on washbowls and bathtubs | ○ | ○ | ○ | ○ | ○ | ○ | ○ | ○ | ○ | ○ | ○ | x |

TABLE 2

|  | Examples | | | | | | Comparative example |
|---|---|---|---|---|---|---|---|
|  | 12 | 13 | 14 | 15 | 16 | 17 | 2 |
| α-Pinene | 0.2 | | 0.1 | | | 0.2 | |
| d-Limonene | | 0.2 | | 0.05 | | | |
| Linalool | | | 0.1 | 0.1 | 0.2 | | |
| Guar gum | 0.5 | | 0.5 | 0.5 | 0.5 | | 0.5 |
| Xanthan gum | | 0.5 | | | | | |
| Glycerin | 1.0 | 1.0 | 1.0 | 1.0 | 1.0 | 3.0 | 1.0 |
| Olive oil | | | | | | 20.0 | |
| Urea | 2.0 | 2.0 | 2.0 | 2.0 | 2.0 | 4.0 | 2.0 |
| Beeswax | | | | | | 2.0 | |
| Sucrose cocoate | 1.0 | | | | | 2.0 | |
| Coconut fatty acid diethanolamide | | 2.0 | 2.0 | 2.0 | 2.0 | | 2.0 |
| Triethanolamine N-cocoyl L-glutamate | | | | 1.5 | 1.5 | | 9.0 |
| Triethanolamine N-cocoyl DL-alanine | 12.0 | 7.5 | 9.0 | 12.0 | 12.0 | | 9.0 |
| Sodium N-stearyol L-glutamate | | | | | | 6.0 | |
| pH in 100 ml aqueous solution | 6.0 | 5.8 | 6.0 | 6.0 | 6.0 | 5.8 | 5.8 |
| Evaluation by patients with atopic dermatitis | ○ | ○ | ○ | ○ | — | ○ | — |
| Evaluation by normals | ○ | ○ | ○ | ○ | ○ | ○ | ○ |
| Evaluation of hair softening and needlessness of rinses | ○ | ○ | ○ | ○ | x | — | x |
| Evaluation of smoothness of the skin | ○ | ○ | ○ | ○ | ○ | ○ | Δ |
| Evaluation of feeling of skin on face being stretched | ○ | Δ | ○ | ○ | ○ | ○ | ○ |
| Evaluation of removal of slime in drain pipes | ○ | ○ | ○ | ○ | ○ | — | x |

In Tables 1 and 2, Example 17 is a cleansing cream and the others are shampoos (including for bath use).

Evaluation Methods

1. Evaluation of hair softening and needlessness of rinses
   Based on a majority's evaluation among seven panelists who used each formulation everyday for a week.
   o: effective; x: unchanged.
2. Evaluation after shampooing
   Based on a majority's evaluation among seven panelists who rubbed off the grime from the body after shampooing and observed whether or not the grime decreased.
   o: effective; x: unchanged.
3. Removal of hair spray deposited on the skin
   Based on a majority's evaluation among seven panelists who shampooed the hair sprayed with a hair spray and checked the odor to determine whether or not it had been removed.
   o: removed by one shampoo; x: not removed by one shampoo.
4. Evaluation of removal of scale on washbowls and bathtubs.
   Based on a majority's evaluation among seven panelists who used each shampoo everyday for a week on already scaled washbowls and bathtubs.

o: scale removed; x: scale left.
5. Smoothness of the skin
Based on a majority's evaluation among seven panelists who used each shampoo everyday for a week.
o: effective; x: unchanged.
6. Feeling of skin on face being stretched
Based on a majority's evaluation among seven panelists who used each shampoo everyday for a week.
o: effective; Δ: somewhat effective; x: unchanged.
7. Slime in drain pipes
Based on a majority's evaluation among seven panelists who used each shampoo everyday for a month in their domestic baths and then determined whether or not the drain pipe was slimy.
o: not slimy; Δ: somewhat decreased slime; x: slimy.
8. Evaluation by patients with atopic dermatitis
Evaluation by thirty patients with atopic dermatitis who used each shampoo everyday for a week.
o: itch or other conditions were improved in a majority of the patients; x: conditions were improved in very few patients.
9. Evaluation by normals with unaffected skin
Thirty panelists with no skin diseases used each shampoo everyday for a week and then, the number of those who declared abnormality was counted.

ADVANTAGES OF THE INVENTION

Essential oil components of the present invention capable of dissolving chemical fine powder were effective to soften the hair. Because of their acidity, they were found to keep the hair acidic and have a rinsing effect. Shampoos of the present invention could sufficiently remove a hair spray deposited on the hair by only one shampooing, contrary to conventional detergents requiring at least two, normally three or four shampoos.

For skin cleaning, the body cleaned with shampoos of the present invention showed the skin smoothed and no grime collected by rubbing. The grime was collected when N-acylamino acid salts were used alone.

When shampoos of the present invention were used in bathtubs, no scale was deposited on either bathtubs or washbowls. This greatly reduces the time for cleaning bathtubs.

Shampoos of the present invention were also found to have the effect of cleaning drain pipes as evident from polished drain pipes free from slime. Shampoos of the present invention can also be used as such as detergents for bathtubs or the like.

What is claimed is:

1. A shampoo composition comprising (a) 0.05–5.0% by weight of an essential oil component selected from the group consisting of pinenes, limonenes and terpinenes, (b) 3.0–20% by weight of an N-acylamino acid salt and (c) 0.1–15.0% by weight of a sucrose fatty acid ester or a $C_6$–$C_{18}$ fatty acid alkylolamide.

2. The shampoo composition of claim 1 further comprising an essential oil component selected from the group consisting of linalool, citronellol, nerol, terpineol, geraniol and cineole in addition to said essential oil component.

3. A skin cleansing cream comprising (a) 0.05–5.0% by weight of an essential oil component selected from the group consisting of pinenes, limonenes and terpinenes, (b) 3.0–20% by weight of an N-acylamino acid salt and (c) 0.1–15.0% by weight of a sucrose fatty acid ester or a $C_6$–$C_{18}$ fatty acid alkylolamide and (d) 10.0–90.0% by weight of a natural liquid oily component or a natural solid oily component.

4. The composition of claim 1, wherein the ratio of said essential oil component to said N-acylamino acid salt is about 1:2 to about 1:120 by weight.

5. The composition of claim 1, wherein the ratio of said essential oil component to said N-acylamino acid salt is about 1:9 to about 1:80 by weight.

6. The composition of claim 1, wherein said essential oil component is included in an amount to disperse fine powders and fats.

7. The composition of claim 1, wherein said essential oil component is included in an amount of about 0.1 wt % to about 1.0 wt %.

8. The composition of claim 1, wherein said N-acylamino acid is included in an amount to solubilize said essential oil component.

9. The composition of claim 1, wherein said N-acylamino acid is included in an amount of about 6.0 wt % to about 15.0 wt %.

10. The composition of claim 1, wherein said sucrose fatty acid ester or fatty acid alkanol amide is included in an amount to solubilize said N-acylamino acid salt.

11. The composition of claim 1, wherein said sucrose fatty acid ester or fatty acid alkanol amide is included in an amount of about 1.0 wt % to about 10.0 wt %.

12. The composition of claim 1, further comprising a polysaccharide in an amount to provide an antioxidant effect to said essential oil component and to increase mildness of said composition.

13. The composition of claim 12, wherein said polysaccharide is included in an amount of about 0.1 wt % to about 2.0 wt %.

14. The composition of claim 1, further comprising about 0.5 wt % to about 10 wt % of a thickener selected from the group consisting of glycerin, sodium lactate, D-sorbitol, and chitin-chitosan.

15. The composition of claim 12, further comprising about 0.5 wt % to about 10 wt % of a citric acid salt dispersion stabilizer.

16. The composition of claim 3, wherein said composition has a ratio of said liquid oily component or solid oily component to an aqueous phase of about 1:9 to about 9:1.

* * * * *